United States Patent [19]

Barton et al.

[11] Patent Number: 5,243,060
[45] Date of Patent: Sep. 7, 1993

[54] SILYLENE-DIETHYNYL-ARYLENE POLYMERS HAVING LIQUID CRYSTALLINE PROPERTIES

[75] Inventors: Thomas J. Barton; Yiwei Ding, both of Ames, Iowa

[73] Assignee: Iowa State University Research Foundation, Inc., Ames, Iowa

[21] Appl. No.: 866,564

[22] Filed: Apr. 10, 1992

[51] Int. Cl.$^5$ .............................................. C07F 7/08
[52] U.S. Cl. .................................... 556/435; 528/15;
528/25; 528/27; 528/29; 546/14; 556/427
[58] Field of Search .................. 556/435, 427; 528/15, 528/25, 27, 29; 546/14

[56] References Cited

U.S. PATENT DOCUMENTS

| 4,940,767 | 7/1990 | Barton et al. ........................ 528/35 |
| 4,965,332 | 10/1990 | Barton et al. ........................ 528/25 |
| 5,072,012 | 12/1991 | Fujiki et al. ........................ 556/435 |
| 5,151,538 | 9/1992 | Hayashi et al. ................ 556/435 X |

FOREIGN PATENT DOCUMENTS

1-062312  3/1989  Japan .

OTHER PUBLICATIONS

R. J. P. Corriu, *J. Polymer Science: Part C: Polymer Letters*, 28, 431–437 (1990).
D. B. DuPre, *Kirk–Othmer Concise Encyclopedia of Chemical Technology*, John Wiley & Sons: New York 1985; pp. 703–705.
Y. Ding et al., Poster entitled "Silylene–Diethynylbenzene Polymers" presented at XXIII Organosilicon Symposium, Midland, Mich., Apr. 20–21, 1990.
Y. Ding et al., Poster entitled "Synthesis of Soluble, Crystalline Silylene–Diethynylbenzene Polymers" presented at XXIV Organosilicon Symposium, El Paso, Tex., Apr. 12–13, 1991.
V. D. Ermakova et al., *Chem. Abstr.*, 88, 24, 88:153350f (1978).

(List continued on next page.)

*Primary Examiner*—Paul F. Shaver
*Attorney, Agent, or Firm*—Merchant, Gould, Smith, Edell, Welter & Schmidt

[57] ABSTRACT

The present invention provides linear organosilicon polymers including diethynyl-(substituted)arylene units, and a process for their preparation. These novel polymers possess useful properties including electrical conductivity, liquid crystallinity, and/or photoluminescence. These polymers possess good solubility in organic solvents. A preferred example is produced according to the following reaction scheme.

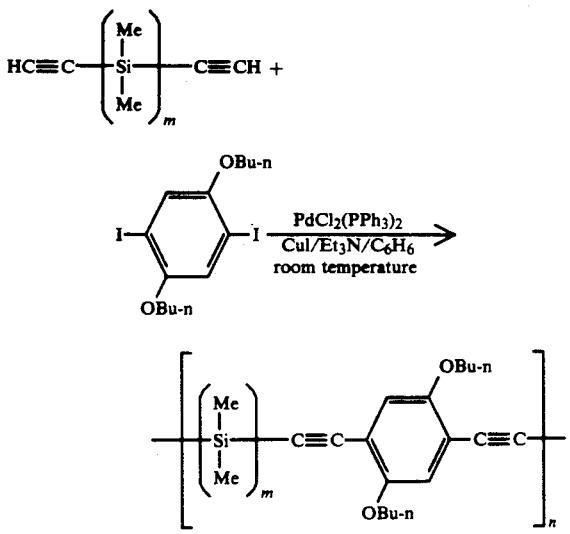

These polymers can be solvent-cast to yield excellent films and can also be pulled into fibers from concentrated solutions. All possess substantial crystallinity as revealed by DSC analysis and observation through a polarizing microscope, and possess liquid crystalline properties.

20 Claims, 8 Drawing Sheets

OTHER PUBLICATIONS

C. C. Frazier et al., *Chem. Abstr.*, 111, 111:105446p (1989).

F. W. Hofmann, *Chem. Abstr.*, 64, Col. 6848 "Acetylenic silicon, arsenic, and mercury derivatives and their polymers" (1966).

R. Giesa et al., *Makromol. Chem.*, 191, 857–867 (1990).

I. M. Gverdtsiteli et al., *Chem. Abstr.*, 77, 520, 77:19723z (1972).

S. Ijadi-Maghsoodi et al., *J. Polym. Sci., Polym. Chem.*, 28, 955–965 (1990).

M. Ishikawa et al., *Chem Abstr.*, 107, 17, 107:199167r (1987).

S. Kajigaeshi et al., *Chemistry Letters*, 795–798 (1988).

Y. Koizumi et al., *Chem. Abstr.*, 105, 63, 105:192460f (1986).

Y. Koizumi et al., *Chem. Abstr.*, 105, 63, 105:192461g (1986).

V. V. Korshak et al., *Izv. Akad. Nauk SSSR*, 4, 728 (1962) (published English translation, p. 677).

M. D. Lewis et al., *Tetrahedron Letters*, 29, 2279–2282 (1988).

H. Q. Liu et al., *Can. J. Chem.*, 68, 1100–1105 (1990).

L. K. Luneva et al., *Vysokomol. Soyed.*, A9, 910–914 (1967) (published English translation by K. A. Allen, pp. 1019–1023).

K. Okuhara, *Bull. Chem. Soc. Jpn.*, 54, 2045–2052 (1981).

T. Sakamoto et al., *Synthesis*, 312–314 (Apr. 1983).

I. W. Shim et al., *J. Organomet. Chem.*, 260, 171–179 (1984).

R. Subramanian et al., *J. Org. Chem.*, 50, 5430–5432 (1985).

S. Takahashi et al., *Macromolecules*, 12, 1016–1018 (1979).

S. Takahashi et al., *Synthesis*, 627–630 (Aug. 1980).

SILYLENE-DIETHYNYL-ARYLENE POLYMERS HAVING LIQUID CRYSTALLINE PROPERTIES

The present invention was made with the support of the U.S. Department of Energy under Contract No. W-7405-ENG-82. The Government has certain rights to this invention.

FIELD OF THE INVENTION

This invention relates to novel silylene-diethynyl-arylene polymers having liquid crystalline properties, and their preparation. Specifically, the present invention relates to novel silylene-diethynyl-(substituted)arylene polymers that exhibit a stable liquid crystalline state.

BACKGROUND OF THE INVENTION

Liquid crystals, i.e., materials with liquid crystalline properties, are "highly anisotropic fluids that exist between the boundaries of the solid and conventional, isotropic, liquid phase." D. B. DuPré, *Kirk-Othmer Concise Encyclopedia of Chemical Technology*, 1985, John Wiley & Sons, pp. 703-705. That is, materials that are in a liquid crystalline state exhibit anisotropic properties, i.e., properties that differ in different directions, such as thermal/electrical conductivity and light transmission. This liquid crystalline state, i.e., anisotropic state, exists between the boundaries of a solid crystalline phase and an isotropic liquid phase for a given material.

Materials that exhibit liquid crystalline properties typically have an elongated, narrow molecular framework. Examples of organic compounds that exhibit such properties are para-n-octyloxybenzoic acid, para-azoxyanisole, 4-(4'-ethoxybenzylideneamino)cinnamate, bis-(4'-n-heptyloxybenzylidene)-1,4-phenylenediamine, and the like. In materials such as these, the molecules exhibit three dimensional, long-range order, with respect to their centers of gravity, while in a solid crystalline phase. While in a liquid crystalline state, however, the molecules in these materials lack order in at least one dimension, while still maintaining significant long-range orientational order. This long-range orientational order is sufficient to impart solid-like properties to the fluid state. That is, the extent of molecular ordering and intermolecular forces in the liquid crystalline state of a liquid crystal is sufficient to impart properties of both a solid and a liquid.

Simply because a molecule is long and narrow, however, does not indicate that the material will possess liquid crystalline characteristics. There must be sufficiently strong forces between the molecules to retain an ordered molecular arrangement upon melting, for example. That is, the intermolecular forces must be sufficient to form regular solids, while at the same time the molecules must be free to move as they do in liquids.

Because the intermolecular forces impart both solid and liquid properties, liquid crystals are sensitive to external changes in temperature, pressure, electric fields, magnetic fields, and the like. Thus, they are extremely useful in devices that monitor such changes, and/or cause an event to occur upon such a change. Liquid crystals are therefore useful in sensors, switches, and shutters, for example.

Liquid crystals are characterized as either thermotropic or lyotropic. That is, liquid crystals are characterized by how the material forms a liquid crystalline state. The liquid crystalline state of thermotropic liquid crystals results from a phase transition from a solid to a liquid crystalline state upon heating. This occurs at the melting point of the material. The liquid crystalline state of lyotropic liquid crystals results from the action of a solvent on the solid. That is, the anisotropic state of a lyotropic liquid crystal exists in solution, whereas the anisotropic state of a thermotropic liquid crystal exists in a melt. The anisotropic state, i.e., the liquid crystalline state, of both a lyotropic liquid crystal and a thermotropic liquid crystal can be converted into an isotropic fluid at sufficiently high temperatures, and for a lyotropic liquid crystal upon dilution. For a thermotropic liquid crystal, this transition occurs at the "clearing" temperature.

Lyotropic liquid crystals can be used to prepare fibers by pulling the fibers out of the solvent. They can also be readily used in the preparation of composite materials. Thermotropic liquid crystals are advantageous and preferred to lyotropic liquid crystals because they do not require the use of an organic solvent and are generally easier to process. Thus, they can be used for a wider variety of products, particularly films and fibers.

Whether thermotropic or lyotropic, there are three distinctive structures that result from the dimensional and packing characteristics of the molecules. These structures are known as the smectic, nematic, and cholesteric structures, and often exhibit further subclasses of structures. A liquid crystalline material may exhibit one or more structures and/or structural subclasses. In thermotropic liquid crystals, for example, transitions between structural subclasses occur as the temperature is varied. These transitions are usually consistent with the gradual breakdown upon heating of long-range molecular order. Frequently, such transitions are reversible upon heating and cooling. Electric and magnetic fields can also induce such transitions.

Because polymeric materials, such as linear polymers, often adopt an elongated configuration, it was generally believed that they could also exhibit liquid crystalline properties. Many polymers, however, are thermally stable, insoluble, or decompose prior to forming a fluid. Thus, it has not generally been possible to demonstrate that polymers can exhibit liquid crystalline characteristics.

Polymers that do exhibit liquid crystalline characteristics, however, can exhibit either lyotropic, thermotropic, or both types of liquid crystalline characteristics, as can molecular liquid crystals. Polymers that exhibit thermotropic liquid crystalline characteristics do so at temperatures in a range between the melting point of the solid and the lower of either the clearing temperature or the decomposition temperature of the material. Such polymers are useful in the production of lightweight, ultrahigh strength, and temperature-resistant fibers. Thus, polymers are needed that exhibit liquid crystalline characteristics, particularly thermotropic liquid crystalline properties.

Polymeric materials, such as certain polyesters, polyethers, polyamides, polyisocyanates, polyphosphazines, and polysiloxanes, exhibit liquid crystalline properties, particularly lyotropic liquid crystalline properties. Polymeric poly(yne) materials containing certain transition metals in the backbone are also known to exhibit lyotropic liquid crystalline properties. For example, —[—Pt(PBu$_3$)$_2$—C≡C—C≡C—]$_n$—, —[—Pt(PBu$_3$)$_2$—C≡C—C$_6$H$_4$—C≡C—]$_n$—, and —[—Pt(PBu$_3$)$_2$—C≡C—C$_6$H$_4$—C≡C—≡C—C$_6$H$_4$—C≡C—]$_n$— have been shown to exhibit lyotropic liquid crystalline properties. See S. Takahashi et al., *Macro-* molecules, 12, 1016 (1979). Although these polymers are soluble and exhibit lyotropic liquid crystalline properties, they decompose before melting and thus do not exhibit thermotropic liquid crystalline properties.

Numerous organosilicon poly(yne) polymers are known. However, none have been reported in the literature to exhibit liquid crystalline properties. For example, silylenediethynylbenzene polymers of the general formula $-[-(SiR_2)_m-C\equiv C-C_6H_4-C\equiv C-]_n-$, wherein m=1-2 and R=H, methyl (Me), and phenyl (Ph), are known. See, for example, Y. Ding and T. J. Barton et al., *XXIII Organosilicon Symposium*, Apr. 20-21, 1990, Midland, Mich.; R. J. P. Corriu, *J. Polymer Science: Part C: Polymer Letters*, 28, 431 (1990); H. Q. Lin et al., *Can. J. Chem.*, 68, 1100 (1990); I. W. Shim et al., *J. Organomet. Chem.*, 260, 171 (1984); and L. K. Luneva et al., *Vysokomol. Soyed.*, A9, 910 (1967). These polymers contain the 1,4-diethynylbenzene unit in the chain, which can potentially impart liquid crystalline properties to the polymers. However, these polymers have not been reported in the literature to display either type of liquid crystalline property. Therefore, a continuing need exists for organosilicon polymers that can exhibit liquid crystalline properties.

SUMMARY OF THE INVENTION

The present invention is directed to linear polymers containing diethynyl-arylene units, preferably 1,4-diethynylphenylene units, wherein there are pendant groups on the arylene moieties in the polymer main chain, and their preparation. These novel linear polymers exhibit liquid crystalline properties, preferably thermotropic liquid crystalline properties. They are also advantageous because they are soluble, which imparts improved processability and the potential for lyotropic liquid crystalline behavior. The present invention is preferably directed to a series of silylene-1,4-diethynyl-(substituted)phenylene polymers, which possess thermotropic liquid crystalline properties.

Thus, the polymers of the present invention are of the general formula: $-[-(SiR^1R^2)_m-C\equiv C-Ar-C\equiv C-]_n-$, and possess a weight average molecular weight of at least about 5,000, wherein $n \geq 2$, m=1-6, each R, i.e., $R^1$ and $R^2$, is independently selected from the group consisting of alkyl, alkenyl, aryl, and aralkyl radicals, i.e., groups, and Ar is a substituted arylene group. By "substituted" arylene (or phenylene), it is meant that the arylene group(s) in the main polymer chain contains at least one pendant functional group that does not interfere with the formation of the linear polymers. The term "arylene" refers to a bis-functional aromatic moiety such as phenylene, biphenylene, naphthylene, thiophenylene, and the like, which contains further pendant groups as noted above.

Preferably, the polymers have a weight average molecular weight of between about 5,000 and about 100,000. More preferably, the polymers have a weight average molecular weight of between about 9,000 and about 40,000. For these polymers, preferably n=2-150, more preferably n=20-90, and most preferably n=40-60. Preferably, m=1-4, and more preferably, m=2 and 4.

Preferably, each $R^1$ and $R^2$ is independently selected from the group consisting of $(C_1-C_{20})$alkyl, $(C_2-C_{20})$alkenyl, $(C_6-C_{17})$aryl, and $(C_7-C_{20})$aralkyl, wherein the alkyl moiety of the aralkyl group is preferably $(C_1-C_6)$alkyl. Most preferably, each $R^1$ and $R^2$ is independently selected from the group consisting of $(C_1-C_6)$alkyl, $(C_2-C_6)$alkenyl, and $(C_6-C_{17})$aryl radicals.

Preferably, arylene is $(C_6-C_{24})$arylene (e.g., phenylene, a fused ring system such as naphthylene, a multiple ring system such as biphenylene, or is a heteroaromatic system, such as a thiophenylene or pyridenylene group), which is substituted with at least one functional group. Representative arylenes are shown in FIG. 8. More preferably, the $(C_6-C_{24})$arylene is a 1,4-phenylene, which is substituted with at least one functional, i.e., pendant, group, preferably two functional groups. If the phenylene moiety has two functional groups, preferably they are in the ortho positions, e.g., 2,3-disubstituted-1,4-phenylene, or para positions, e.g., 2,5-disubstituted-1,4-phenylene.

The term "alkyl" means a saturated linear, branched, or cyclic hydrocarbon group. The term "alkenyl" means an unsaturated linear, branched, or cyclic hydrocarbon group. The term "aryl" means a mononuclear or polynuclear aromatic hydrocarbon or heteroaromatic group. The term "aralkyl" means a linear, branched, or cyclic alkyl hydrocarbon group having at least one mononuclear or polynuclear aromatic or heteroaromatic substituent. The term "polymeric" or "polymer" is used herein in its usual manner to mean a compound consisting essentially of repeating structural units. The term "linear" polymer means a polymer whose molecules are arranged in a chain-like fashion with few (or no) branches or bridges between the chains.

C.) of —[—(SiMe$_2$)$_4$—C≡C—[C$_6$H$_4$(OMe)$_2$]—C≡C—]$_n$- at a heating rate of 10° C./minute (melting point =86.31° C.; clearing temperature =109.95° C.).

Figure 8:
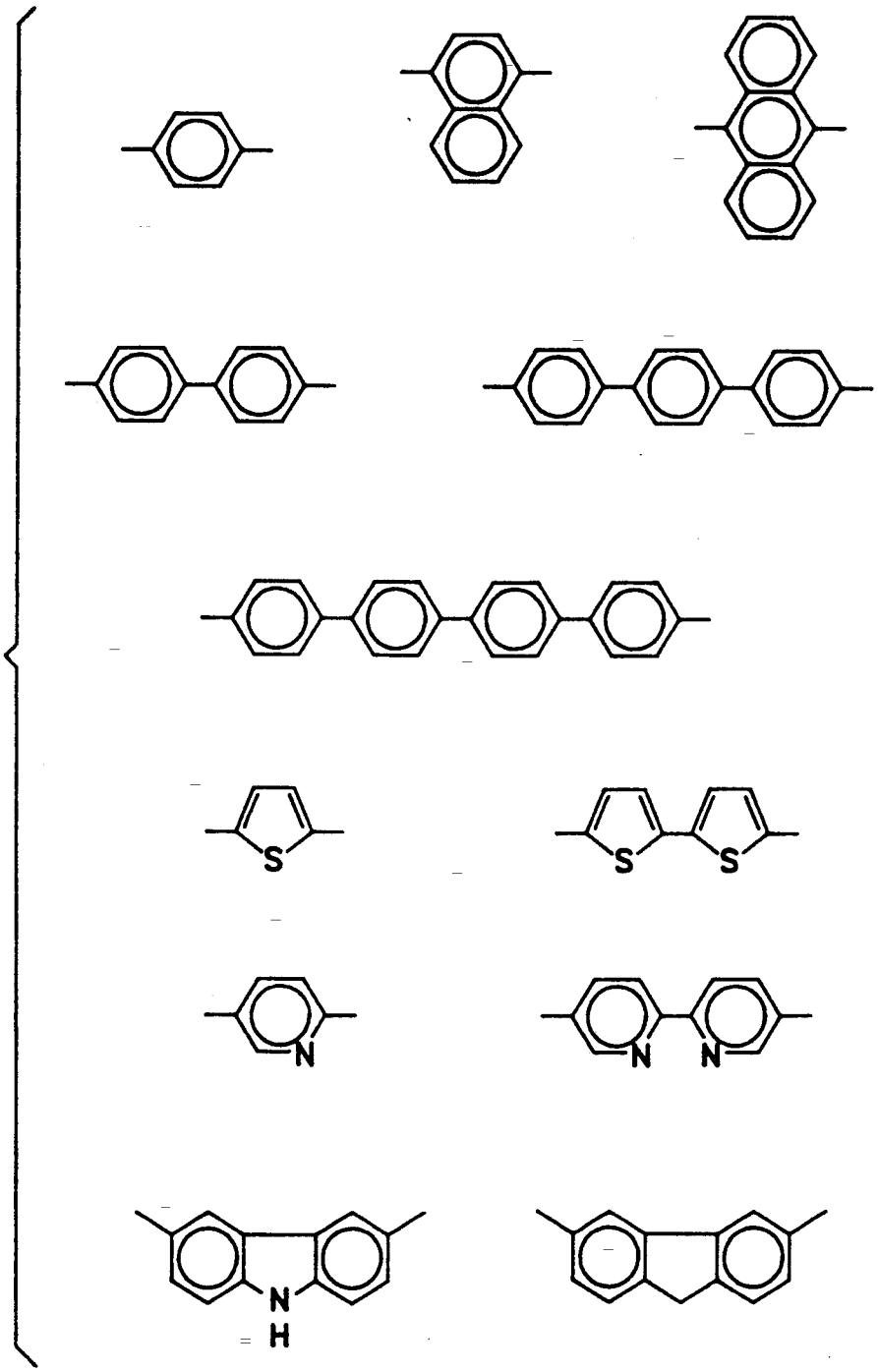

FIG. 8 is a list of possible representative arylenes, i.e., bis-functional aromatic moieties. These arylenes are also functionalized with at least one pendant group (not represented).

DETAILED DESCRIPTION OF THE INVENTION

The present invention is based upon the discovery that novel organosilicon linear polymers containing diethynyl-(substituted)arylene units possess liquid crystal properties. These polymers are referred to herein as organosilicon liquid crystals. Specifically, the present invention is directed to novel silylene-diethynyl-(substituted)arylene polymers that can attain a stable thermotropic liquid crystalline state. The polymers of the present invention generally possess considerable crystallinity as revealed by Differential Scanning Calorimetry (DSC) analysis and polarized microscopy. These polymers are thus useful as liquid crystalline materials that find applications in the optoelectronics and related industries. For example, these polymers can be used in television displays, oscillographic displays, optical printer heads, optical switches, pressure sensors, and the like.

The polymers of the present invention possess, or can be readily modified to possess, additional unique properties including electrical conductivity, luminescence, and photoconductivity. The polymers of the present invention are also soluble in organic solvents. As a result, these polymers can be solvent-cast to excellent films and pulled into fibers from concentrated solutions, if desired.

The organosilicon polymers of the present invention are represented by the formula —[—(SiR$^1$R$^2$)$_m$—C≡C—Ar—C≡C—]$_n$-, wherein n≥2, m=1-6, Ar is a substituted arylene moiety, and each R$^1$ and R$^2$ is independently selected from the group consisting of alkyl, alkenyl, aryl, and aralkyl radicals. Examples of suitable R$^1$ and R$^2$ groups include, but are not limited to, methyl, ethyl, propyl, butyl, pentyl, hexyl, heptyl, octyl, phenyl, and vinyl groups.

The preferable polymers have a weight average molecular weight of at least about 5,000. These polymers are more easily processed, e.g., pulled into fibers, than are polymers of lower weight average molecular weight. Preferably, the number of recurring units in the polymer, i.e., "n," is between 2 and about 150, more preferably n=20-90, and most preferably n=40-60. Preferably, the number of recurring SiR$_2$ units in the polymer, i.e."m," is between 1 and about 4, preferably m=2 and 4.

More preferably, the organosilicon polymers, i.e., organosilicon liquid crystals, of the present invention have a weight average molecular weight of between about 5,000 and about 100,000. More preferably, they have a weight average molecular weight of between about 9,000 and about 40,000. Preferably, these organosilicon polymers possess a polydispersity, which is a measure of the molecular weight dispersity, i.e., nonhomogeneity, within the system, of about 1.2 to about 3.0. More preferably, it is about 1.7-2.2, and most preferably about 1.9-2.1. The polydispersity is determined by the ratio of the weight average molecular weight (Mw) to the number average molecular weight (Mn).

Preferably, each of the substituents, i.e., R groups, in these organosilicon polymers is independently selected from the group consisting of (C$_1$-C$_{20}$)alkyl, (C$_2$-C$_{20}$)alkenyl, (C$_6$-C$_{17}$)aryl, and (C$_7$-C$_{20}$)aralkyl, wherein the alkyl moiety of the aralkyl group is preferably (C$_1$-C$_6$)alkyl. More preferably, each R$^1$ and R$^2$ is independently selected from the group consisting of (C$_1$-C$_6$)alkyl, (C$_2$-C$_6$)alkenyl, and (C$_6$-C$_{17}$)aryl radicals.

Preferably the arylene group is a (C$_6$-C$_{24}$)arylene, substituted with at least one functional group. This can include, for example, phenylene, fused ring systems such as naphthylene, multiple ring systems such as biphenylene, or hetero-aromatic systems such as a thiophenylene or pyridenylene group or mixtures thereof. Representative examples of arylenes, i.e., bis-functional aromatic moieties, are shown in FIG. 8 (without any pendant groups represented). More preferably, the (C$_6$-C$_{24}$)arylene is a 1,4-phenylene, which is substituted with at least one functional, i.e., pendant, group.

A wide variety of functional groups, i.e., substituents, can be present on the arylene moieties, including (C$_1$-C$_6$)alkyl, (C$_1$-C$_6$)alkoxy, (C$_2$-C$_6$)alkenyl, (C$_6$-C$_{17}$)aryl, F, Cl, amino, nitro, and the like. Preferably, the arylene (e.g., phenylene) moieties are functionalized with pendant groups, i.e., substituents, selected from the group consisting of (C$_1$-C$_6$)alkyl, (C$_1$-C$_6$)alkoxy, or mixtures thereof. More preferably, the pendant groups are selected from the group consisting of (C$_2$-C$_6$)alkyl, (C$_2$-C$_6$)alkoxy, or mixtures thereof. These larger groups are advantageous because they are believed to hinder crosslinking and/or decomposition of the polymers at elevated temperatures.

The substituted arylene is preferably monosubstituted or disubstituted, preferably it is disubstituted, i.e., contains two pendant groups. For a fused ring or multiple ring system, this does not necessarily mean that every ring in the system must be disubstituted, however. For optimum formation of linear polymers, these two pendant groups are in an ortho- or para- relationship. For example, preferred 1,4-phenylenes are 2,3-disubstituted-1,4-phenylene (ortho substituted, and 2,5-disubstituted-1,4-phenylene (para substituted).

The polymers of the present invention are generally soluble in organic solvents such as chloroform (CHCl$_3$), benzene ("Bz"), toluene, tetrahydrofuran (THF), and the like. The solubilities of the polymers are typically at least about 5 grams per liter; however, this varies depending on the pendant groups and the solvents chosen. The polymers of the present invention can be pulled into fibers, cast into films, molded into monolithic forms, and prepared as powders or coatings, as well as formed into numerous preselected shapes.

The process for preparing the organosilicon polymeric liquid crystals of the present invention involves the catalyzed condensation polymerization of diethynylsilane monomers of the general formula HC≡C—(—SiR$^1$R$^2$)$_m$—C≡CH, wherein m, R$^1$, and R$^2$, are as described above, and para-dihalo substituted arylene monomers of the general formula X-Ar-X (wherein X is preferably Br and I, and Ar is an arylene group as described above). The polymerization reaction involves a carbon-carbon bond coupling reaction, which can be represented by the following generalized scheme:

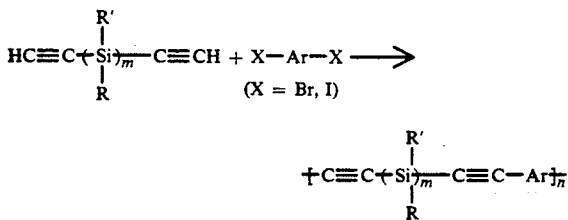

A typical example involves the reaction of diethynyldimethylsilane (m=1, R and R'=Me) with 1,4-dibutoxy-2,5-diiodobenzene. The diethynylsilanes are readily available from the condensation of an acetylenic Grignard reagent, HC≡C—MgX (wherein X is Cl, Br or I), and the corresponding dichlorosilane (dichlorodisilane, dichlorotrisilane, dichlorotetrasilane). A representative example of this preparation is presented in Experimental Example 3. The para-dihalo substituted arylene monomers (X-Ar-X) are readily available from routine synthetic reactions, as represented by Experimental Example 4.

This process provides a convenient, high-yield, route to the polymers of the present invention. The process is conducted in the presence of a transition metal complex capable of catalyzing a carbon-carbon coupling reaction. It can be carried out with or without an external heat source. It can be carried out neat, or in solution. It uses two different reagents, i.e., monomers in an approximate equimolar ratio, and typically requires no product separation step because no significant by-products are generally produced.

The process of the present invention can be very efficient, resulting in product yields of greater than about 50%, often greater than about 60%, and more often greater than about 70%. Furthermore, the structural purity of the polymers produced by the process of the present invention is typically greater than about 90%, often greater than about 95%, and can be as high as 99.5%, as evidenced by nuclear magnetic resonance spectroscopy. That is, the process of the present invention is advantageous at least because it is simple and produces the linear polymers in high yields and high structural purity.

The synthesis of the linear polymers of the present invention is conducted in the presence of a condensation catalyst, particularly a transition metal catalyst of Groups 8, 9, and 10 (formerly classified as the Group VIIIB or platinum group metals). These include catalysts containing at least one of the following metals: Fe, Ru, Os, Co, Rh, Ir, Ni, Pd, and Pt. The catalyst can be homogeneous or heterogeneous. Preferably, it is a soluble homogeneous catalyst or catalyst system. Although any of the established carbon-carbon coupling catalysts or catalyst systems can be employed, the synthetic procedure is not limited to the use of these catalysts.

Preferably, the catalyst is a palladium catalyst. More preferably, the catalyst is a Pd(II) or a Pd(0) catalyst, such as bis(triphenylphosphine)palladium(II) chloride, bis(triphenylphosphine)palladium(II) acetate, bis(dibenzylidene-acetone)palladium(0), bis(isonitrile)palladium(0), bis(tert-butyl-isonitrile)palladium(0), bis(p-tolylisonitrile)palladium(0),bis(phenyl-isonitrile)palladium(0), bis(p-methoxyphenyl-isonitrile)palladium(0), and the like. Of these catalysts, bis(triphenylphosphine)-palladium(II) chloride (PdCl$_2$(PPh$_3$)$_2$) and bis(triphenylphosphine)palladium(II) acetate (Pd(CH$_3$COO)$_2$(PPh$_3$)$_2$) are preferred. Most preferably, the catalyst is PdCl$_2$(PPh$_3$)$_2$.

In addition to this catalyst, the process for preparing the polymers of the present invention preferably employs a Cu(I) or a Cu(II) cocatalyst. The Cu(I) or Cu(II) cocatalyst is preferably a copper(I) halide (CuX) or a copper(II) halide (CuX$_2$). The halide is preferably Cl, Br, I. Most preferably, the cocatalyst is CuCl, CuBr, or CuI. Generally, the molar ratio between the copper cocatalyst and the palladium catalyst, for example, is approximately 1:1.

In the process of preparing the organosilicon polymers of the present invention, an amount of the catalyst effective to catalyze the polymerization of the monomers is used. This can vary significantly, but preferably an amount is used that will produce the polymers in high yields, i.e., greater than about 50% yields, within a short period of time, i.e., about 2 hours. The time of the reaction, however, can vary significantly because it depends on the type of monomers, the concentration of monomers in solution, the amount of catalysts, and the reaction temperature. Preferably, an "effective amount" of a catalyst is at least about 0.5 mole-% of the diethynylsilane monomer. More preferably, the amount of the catalyst used is within a range of about 1 mole-% to 5 mole-% of the diethynylsilane monomer. Generally, about 2 mole-% of the catalyst relative to the diethynylsilane monomer will produce yields of at least about 50%. In embodiments in which a copper cocatalyst is used, these amounts represent the amount of cocatalyst as well. That is, an "effective amount" of a cocatalyst is at least about 0.5 mole-% of the diethynylsilane monomer.

The reaction can be carried out neat, or in the presence of an organic solvent or mixture of solvents. The use of a solvent is typically governed by the reactivity of the monomers. For example, if the monomers are reactive and produce an exothermic reaction, a solvent can be used to moderate the reaction. When a solvent is employed for advantage, it can be any suitable inert organic solvent. Preferably, the solvent is a hydrocarbon solvent. More preferably, the solvent is benzene, toluene, xylene, hexane, or a mixture thereof. Most preferably, the solvent is benzene.

The reaction mixture preferably contains an amine for the purpose of complexing the hydrogen halide generated in situ. This amine can be a secondary amine such as diethylamine, or a tertiary amine such as triethylamine, 1,5-diazabicyclo[4,3,0]non-5-ene, and 1,8-diazabicyclo[5,4,0]undec-7-ene.

The reaction is preferably carried out while the materials are stirred or otherwise agitated. For best results, anhydrous reaction conditions are used. That is, it is advantageous to carry out the reaction in a dry inert atmosphere, such as nitrogen or argon, to prevent the introduction of water or oxygen into the reaction vessel.

The preparation of the polymer can be carried out for as little as 2 hours at room temperature, or without the addition of heat from an external heat source. Preferably, the reaction is carried out over a period of about 2 hours to about 24 hours. The reaction mixture can also be heated to the refluxing temperature of the solvent chosen to complete the polymerization. Preferably, this is a temperature of about 50°–70° C.

The polymerization reaction typically produces a partially crystalline polymer. To increase the molecular weight of the polymer and improve its mechanical properties, additives that controllably crosslink the polymers can be introduced into the reaction mixture in preferred embodiments. Examples of such additives include triiodobenzene, triethynylsilane, and the like.

The polymer produced in the reaction mixture can be easily purified and dried by conventional techniques. For example, the product of the reaction can be precipitated from solution using a solvent in which the polymer is not soluble, such as, for example, methanol. The product can then be filtered and dried under a vacuum. Other separation techniques will be apparent to those skilled in the art. It is not necessary, however, that all solvent or catalyst be removed after the polymerization step.

The following examples are offered to further illustrate the various specific and preferred embodiments and techniques. It should be understood, however, that many variations and modifications may be made while remaining within the scope of the present invention.

Experimental Examples

Polymer Characterization

Infrared spectra were obtained from KBr pellets and recorded on an IBM Model IR/98 FTIR. $^1$H, $^{13}$C, and $^{29}$Si NMR spectra were obtained from CDCl$_3$ solutions and recorded on both Nicolet Model NT-300 MHz and VXR-300 MHz FT spectrometer. Molecular weights were obtained by gel permeation chromatography (GPC) with retention times calibrated against nine narrow-dispersity polystyrene samples (Polymer Labs, Amhurst, Mass.). GPC analyses were performed on a Beckman liquid chromatograph equipped with an R401 RI detector from Waters Associates (Milford, Mass.). Five μ-Styrogel columns (10$^6$, 10$^5$, 10$^4$, 10$^3$, and 500 Å) were employed in series with a THF flow rate of 1 mL/min. These columns are commercially available from Waters Associates (Milford, Mass.), Polymer Labs (Amhurst, Mass.), and Beckman (San Ramon, Calif.). Thermogravimetric analyses (TGA) were performed on a DuPont Model 951 thermal analyzer. Differential Scanning Calorimetry (DSC) analyses were performed on a DuPont Model 910 differential scanning calorimeter. Photographs of the liquid crystalline states were taken on a Leitz Wetzlar Diarux Polarizing Microscope.

EXAMPLE 1

Preparation of Butoxy-Substituted Silylene-Diethynylbenzene Polymers

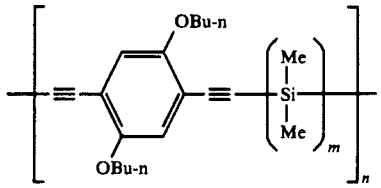

Diethynyldimethylsilane (HC≡C—SiMe$_2$—C≡CH, prepared as shown below in Example 3, 0.352 g, 3.26 mmol) was combined at room temperature with 1,4-dibutoxy-2,5-diiodobenzene (prepared below as shown in Example 4, 1.544 g, 3.26 mmol) in a mixture of benzene (10 mL) and triethylamine (10 mL) containing a catalytic amount of PdCl$_2$(PPh$_3$)$_2$ (available from Aldrich Chemical Co., 23 mg, 3.26×10$^{-2}$ mmol) and CuI (available from Aldrich Chemical Co., 6.2 mg, 3.26×10$^{-2}$ mmol). The mixture was stirred for 24 hours without the addition of heat from an external heat source. The polymer was isolated by filtration and precipitation from MeOH. The polymer was dissolved in THF and reprecipitated from MeOH again. After drying, 0.75 g polymer was collected. A high molecular weight polymer (m =1) was produced in good yield (71%). Polymerization results are summarized in Table I for this polymer as well as those in which m=2–4. The polymers for which m=2–4 were prepared by an analogous method using the following starting monomers:

HC≡C—SiMe$_2$—SiMe$_2$—C≡CH for m=2;

HC≡C—SiMe$_2$—SiMe$_2$—SiMe$_2$—C≡CH for m=3; and

HC≡C—SiMe$_2$—SiMe$_2$—SiMe$_2$—C≡CH for m=4.

TABLE I

| Polymer Structure | Yield | Reaction Time (h) | $M_w \times 10^{-3}$ | $M_w/M_n$ | Solubility |
|---|---|---|---|---|---|
| m = 1 | 71% | 24 | 10.7 | 1.85 | Bz$^a$, CHCl$_3$, THF |
| m = 2 | 88% | 24 | 36.0 | 2.10 | Bz, CHCl$_3$, THF |
| m = 3 | 50% | 100 | 14.0 | 1.82 | Bz, CHCl$_3$, THF |
| m = 4 | 82% | 100 | 15.7 | 2.11 | Bz, CHCl$_3$, THF |

$^a$Benzene.

The molecular weights were obtained by GPC, which in each case showed only a single peak with a polydispersity of approximately 2. In each case UV absorption in THF solution occurred at 360-365 nm (very similar to the absorption maxima of Me$_3$Si—C≡C—C$_6$H$_2$(OBu)$_2$—C≡C—SiMe$_3$). This revealed no evidence for significant extended conjugation in solution.

Figure 1A:
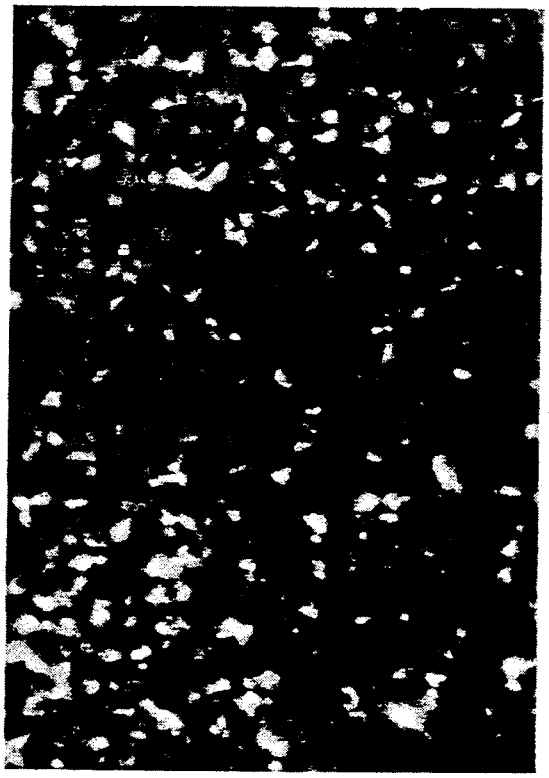
FIG. 1(A) and 1(B) display cross polarization microscopic photographs of the lyotropic liquid crystalline state of $-[-(SiMe_2)-C\equiv C-[C_6H_4(O-n-Bu)_2]-C\equiv C-]_n$- in diphenyl ether at 150° C.
Figure 1B:
Figure 2A:
FIG. 2 displays cross polarization microscopic photographs of the liquid crystalline state of $-[-(SiMe_2)_3-C\equiv C-[C_6H_4(O-n-Bu)_2]-C\equiv C-]_n-$ at 37 °C. while cooling from the isotropic melt. 2(A) was taken immediately after the application of pressure. 2(B) was taken 5 minutes after the removal of pressure.
Figure 2B:
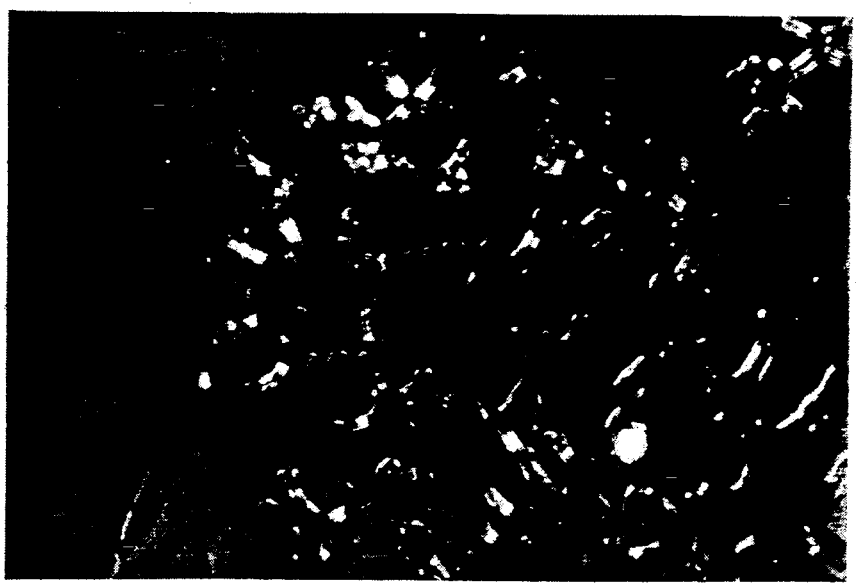
Figure 3:
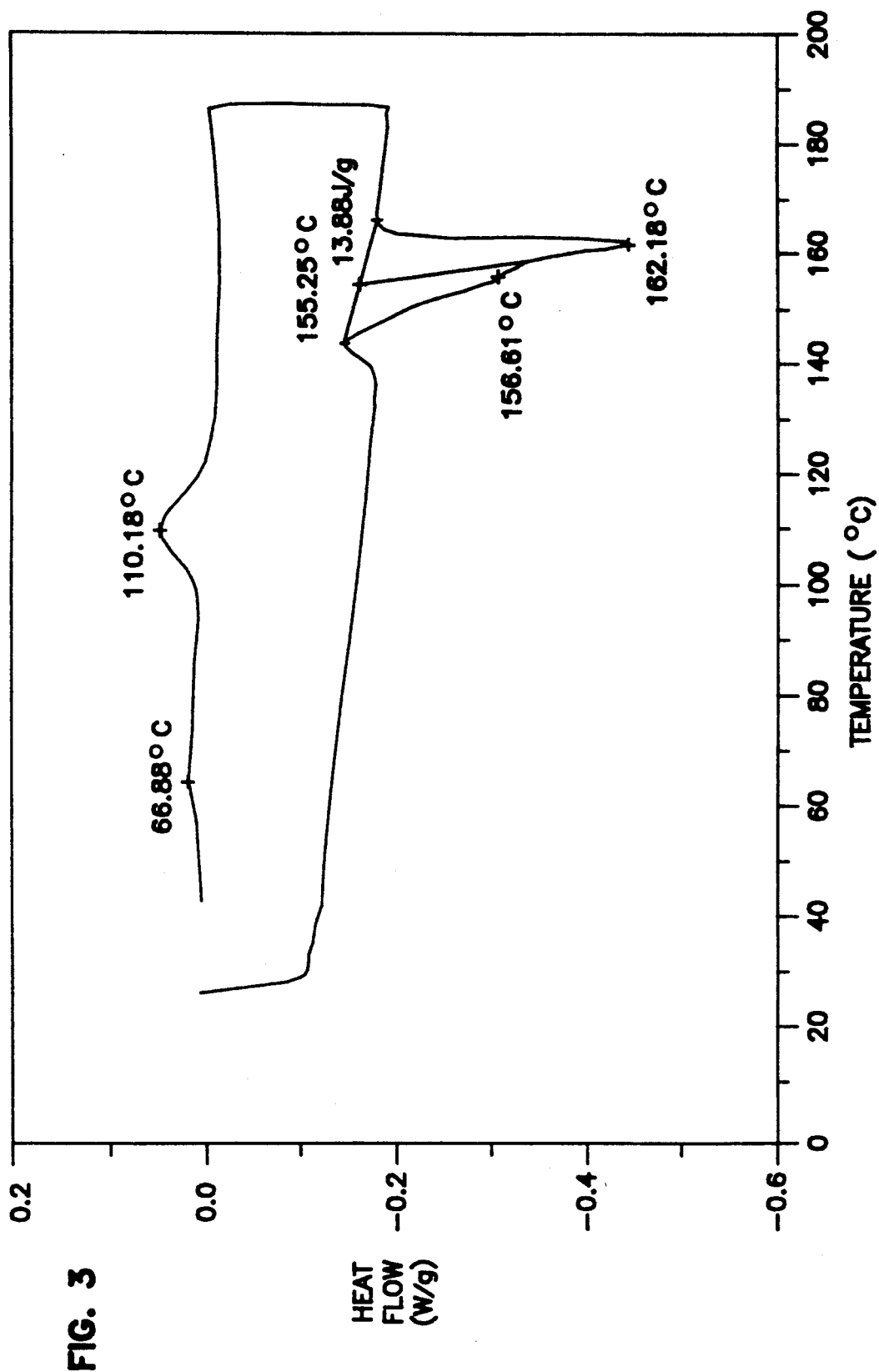
FIG. 3 displays the Differential Scanning Calorimetric scan (heat flow in Watts/gram vs. temperature in °C.) of $-[-(SiMe_2)_2-C\equiv C-[C_6H_4(O-n-Bu)_2]-C\equiv C-]_n-$ at a heating rate of 10° C./minute (melting point =156.61° C.; clearing temperature =162.18° C.).
Figure 4:
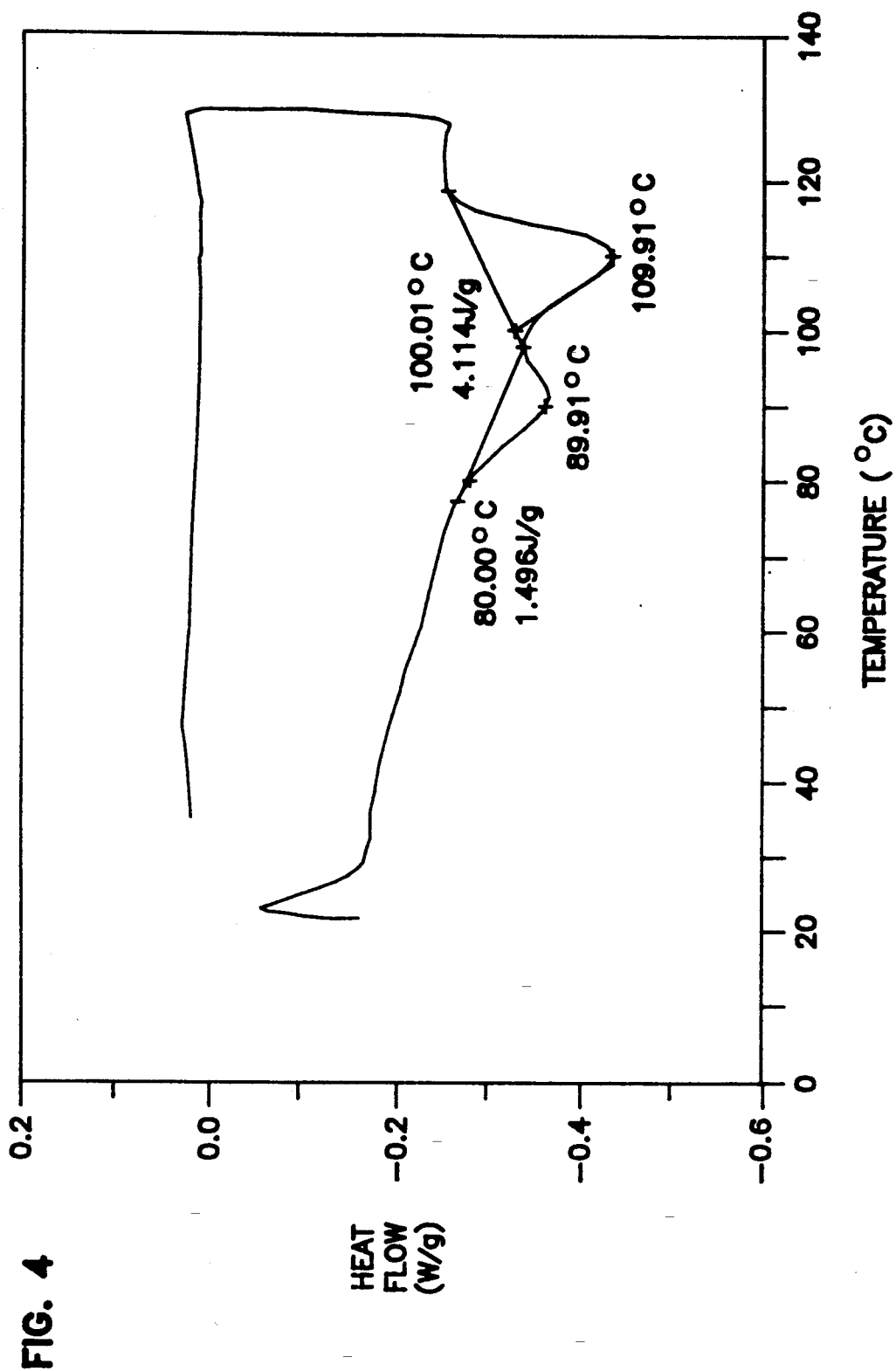
FIG. 4 displays the Differential Scanning Calorimetric scan (heat flow in Watts/gram vs. temperature in °C.) of $-[-(SiMe_2)_4-C\equiv C-[C_6H_4(O-N-Bu)_2]-C\equiv C-]_n-$ at a heating rate of 10° C./minute (melting point =89.91° C.; clearing temperature =109.91° C.).
Figure 5A:
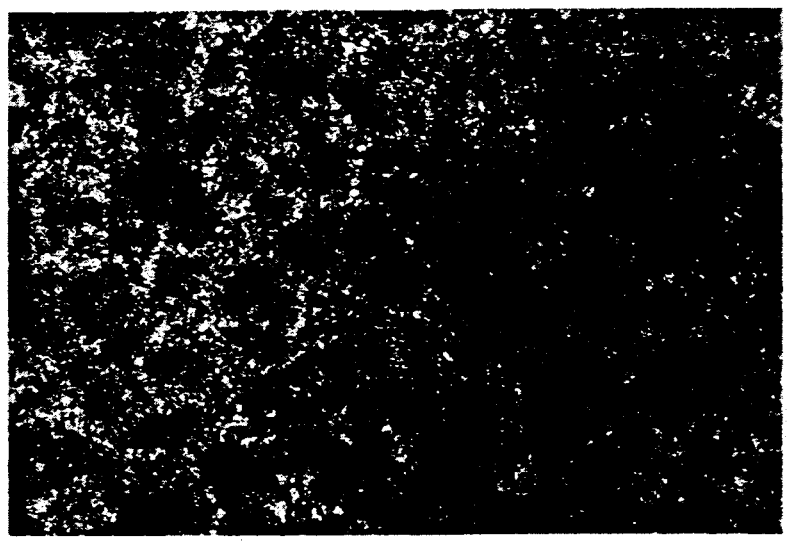
FIG. 5 displays cross polarization microscopic photographs of the liquid crystalline state of $-[-(SiMe_2)_2-C\equiv C-[C_6H_4(O-n-Bu)_2]-C\equiv C-]_n-$ upon cooling from the isotropic melt. 5(A) was taken after the material was cooled to 130° C. (nematic structure). 5(B) was taken after slowly cooling the material to 120° C. (presumably nematic structure and crystallization). 5(C) was taken upon standing at 120° C.
Figure 5B:
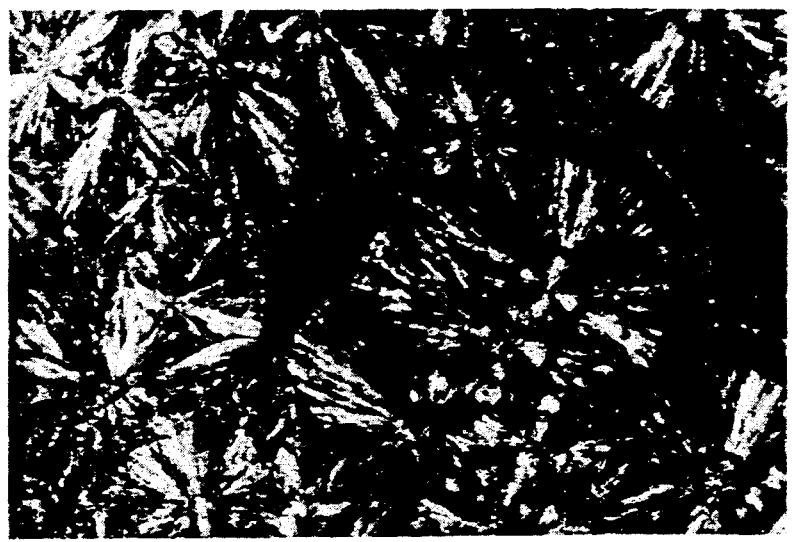
Figure 5C:
Figure 6A:
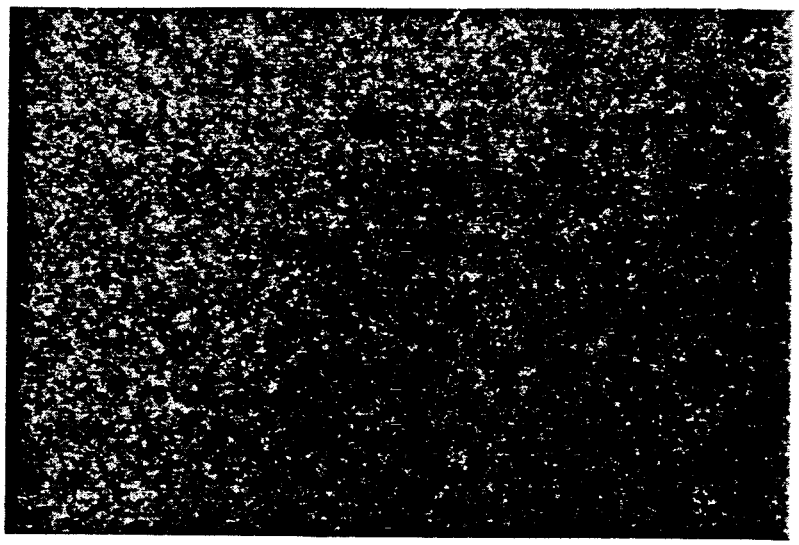
FIG. 6 displays cross polarization microscopic photographs of the liquid crystalline state of $-[-(SiMe_2)_4-C\equiv C-[C_6H_4(O-n-Bu)_2]-C\equiv C-]_n-$ upon cooling from the isotropic melt. 6(A) was taken after the material was cooled to 90° C. (nematic structure). 6(B) and 6(C) were taken after the material was cooled to 85° C. (mosaic texture).
Figure 6B:
Figure 6C:
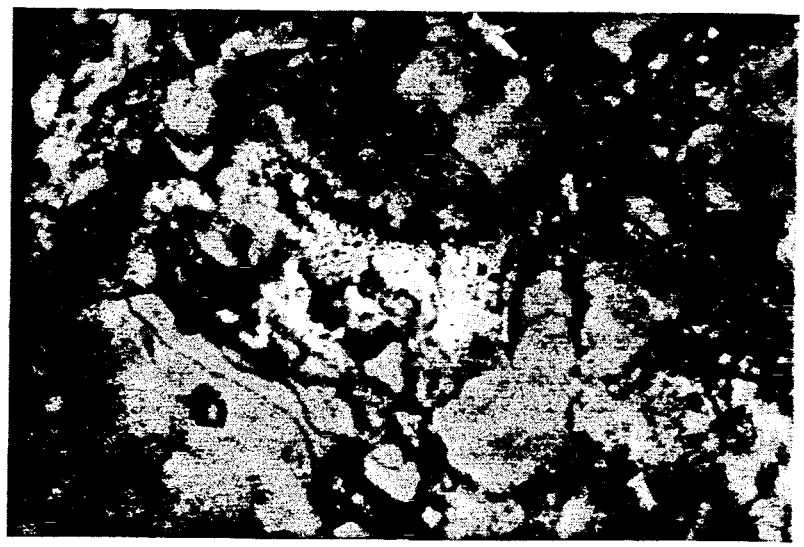

DSC analysis of the polymers revealed interesting differences in thermal behavior. The polymer with only one silicon in the main chain (m=1) showed only a single endothermic peak. No liquid crystalline phase was observed by polarized microscopy either on heating to 100° C. or cooling to 50° C.; however, after heating to 150° C. for 30 minutes apparent crosslinking occurred. The swollen polymer in diphenyl ether showed Schlieren texture, which is indicative of an anisotropic state, i.e., a partially ordered structure, by polarized microscopy (FIG. 1, lyotropic liquid crystalline state). Examination of the polymer with three silicons in the main chain (m=3) was complicated due to its low melting/clearing temperature(s). Polarized microscopic analysis has revealed evidence of a pressure dependent liquid crystallinity, however (FIG. 2, thermotropic liquid crystalline state). The DSC plots for the polymers with two or four silicons in the chain each showed two endotherms and clearly displayed thermotropic liquid crystalline behavior upon melting (FIGS. 3 and 4). Polarized microscopic analysis further evidences this liquid crystalline behavior (FIGS. 5 and 6).

Figure 7:
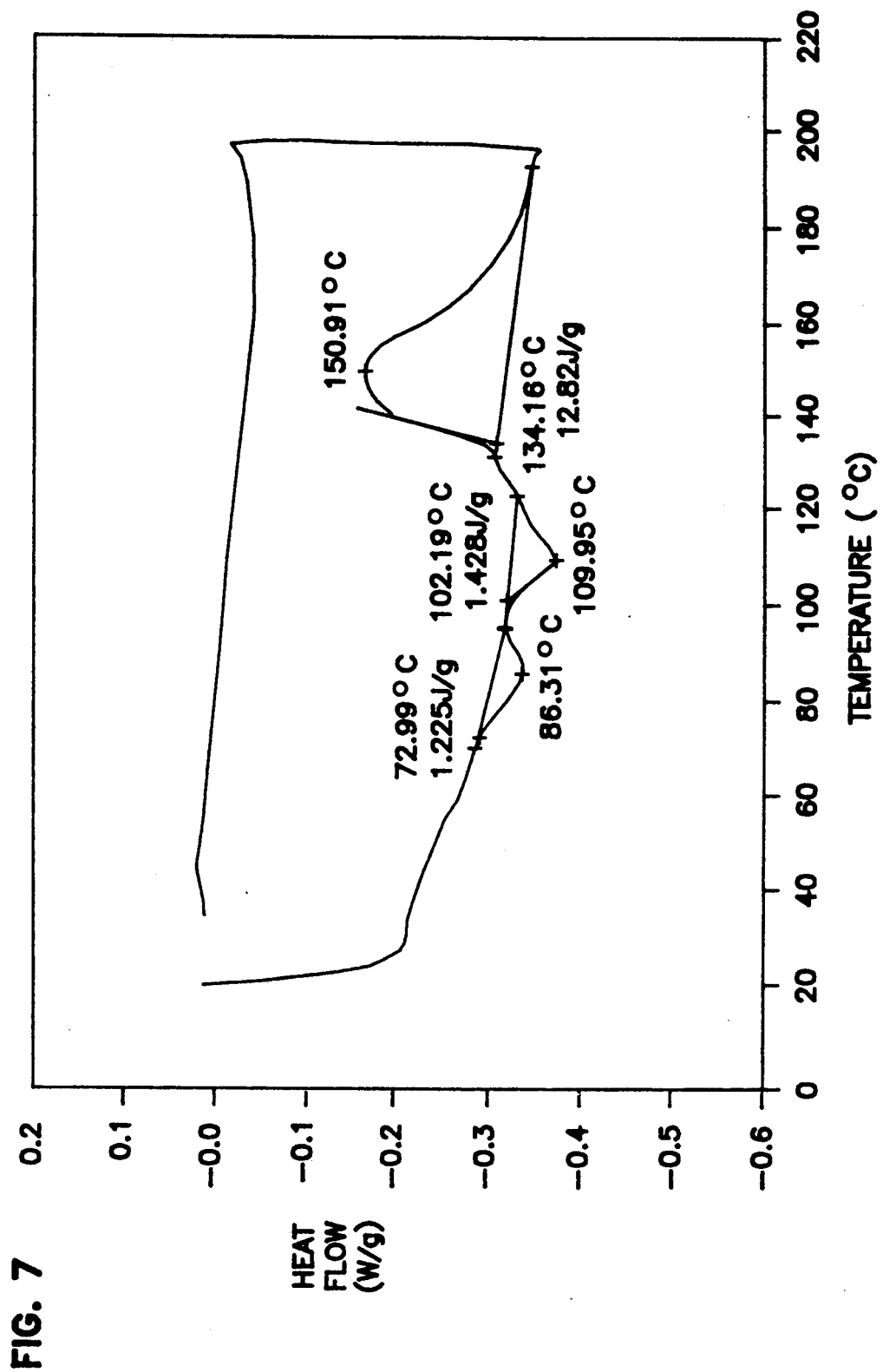
FIG. 7 displays the Differential Scanning Calorimetric scan (heat flow in Watts/gram vs. temperature in °

The effect of the substituent's size is demonstrated by comparing the DSC plots of the polymers with m=4 and n-butoxy or methoxy substituents (FIGS. 4 and 7). In addition to the two endothermic peaks, FIG. 7 shows an exothermic peak at about 151° C., which is believed to be due to crosslinking and/or decomposition. These figures suggest that bulky pendant groups allow liquid crystalline behavior to "match" higher temperatures. That is, the bulkier substituents on the aryl groups produce polymers that display liquid crystalline properties before the polymers melt or decompose. Although not intending to be limited by any theory, it is believed that this is because the bulkier substituents prevent crosslinking or decomposition upon heating.

The characterization data for the polymer prepared by this method when m=4 is as follows. FT-IR: 2959 cm$^{-1}$, 2874 cm$^{-1}$, 2147 cm$^{-1}$, 1497 cm$^{-1}$, 1468 cm$^{-1}$, 1406 cm$^{-1}$, 1275 cm$^{-1}$, 1246 cm$^{-1}$, 1202 cm$^{-1}$, 1067 cm$^{-1}$, 1028 cm$^{-1}$, 905 cm$^{-1}$, 889 cm$^{-1}$, 803 cm$^{-1}$, 777 cm$^{-1}$, 731 cm$^{-1}$. $^1$H NMR: δ6.81 ppm (singlet, 2 H), 3.87 ppm (triplet, 4H), 1.70 ppm (multi, 4H), 1.47 ppm (multi, 4H), 0.904 ppm (triplet, 6H), 0.275 ppm (singlet, 12H), 0.230 ppm (singlet, 12H). $^{13}$C NMR: δ-5.89 ppm (4 1C), -1.85 ppm (4C), 13.87 ppm (2C), 19.25 ppm (2C), 31.34 ppm (2C), 69.02 ppm (2C), 99.2 ppm (2C), 103.66 ppm (2C), 114.03 ppm (2C), 117.10 ppm (2C), 153.76 ppm (2C). $^{29}$Si NMR: δ-33.43 ppm (2 Si), -43.57 ppm (2 Si).

The characterization data for the polymer prepared by this method when m=3 is as follows. FT-IR: 2959 cm$^{-1}$, 2874 cm$^{-1}$, 2147 cm$^{-1}$, 1497 cm$^{-1}$, 1468 cm$^{-1}$, 1406 cm$^{-1}$, 1275 cm$^{-1}$, 1246 cm$^{-1}$, 1202 cm$^{-1}$, 1067 cm$^{-1}$, 1028 cm$^{-1}$, 905 cm$^{-1}$, 810 cm$^{-1}$, 783 cm$^{-1}$, 773 cm$^1$. $^1$H NMR: δ6.82 ppm (singlet, 2H), 3.82-3.94 ppm (triplet, 4H), 1.65-1.80 ppm (multiplet, 4H), 1.35-1.55 ppm (multiplet, 4H), 0.85-1.00 ppm (triplet, 6H), 0.310 ppm (singlet, 12H), 0.255 ppm (singlet, 6H). $^{13}$C NMR: δ-6.93 ppm (2C), -2.00 ppm (4 C), 13.87 ppm (2 C), 19.25 ppm (2C), 31.34 ppm (2C), 69.06 ppm (2C), 99.00 ppm (2C), 103.65 ppm (2C), 114.05 ppm (2C), 117.18 ppm (2C), 153.77 ppm (2C). $^{29}$Si NMR: -33.94 ppm (2 Si), -46.33 ppm (Si).

The characterization data for the polymer prepared by this method when m=2 is as follows. FT-IR: 2959 cm$^{-1}$, 2872 cm$^{-1}$, 2147 cm$^{-1}$, 1497 cm$^{-1}$, 1468 cm$^{-1}$, 1406 cm$^{-1}$, 1275 cm$^{-1}$, 1246 cm$^{-1}$, 1204 cm$^{-1}$, 1067 cm$^{-1}$, 1028 cm$^{-1}$, 906 cm$^{-1}$, 889 cm$^{-1}$, 791 cm$^{-1}$, 773 cm$^{-1}$, 771 cm$^{-1}$. $^1$H NMR: δ0.35 ppm (singlet, 12H), 0.91 ppm (triplet, 6H), 1.40-1.50 ppm (multiplet, 4H), 1.66-1.76 ppm (multiplet, 4H), 3.82-2.92 ppm (triplet, 4H), 6.83 ppm (singlet, 2H). $^{13}$C NMR: δ−2.94 ppm (4C), 13.86 ppm (2C), 19.25 ppm (2C), 31.33 ppm (2C), 69.08 ppm (2C), 98.03 ppm (2C), 103.68 ppm (2C), 113.99 ppm (2C), 117.15 ppm (2C), 153.87 ppm (2C). $^{29}$Si NMR: −37.03 ppm (2 Si).

The characterization data for the polymer prepared by this method when m=1 is as follows. FT-IR: 2959 cm$^{-1}$, 2876 cm$^{-1}$, 2156 cm$^{-1}$, 1499 cm$^{-1}$, 1468 cm$^{-1}$, 1408 cm$^{-1}$, 1277 cm$^{-1}$, 1250 cm$^{-1}$, 1204 cm$^{-1}$, 1067 cm$^{-1}$, 1026 cm$^{-1}$, 976 cm$^{-1}$, 891 cm$^{-1}$, 818 cm$^{-1}$. $^1$H NMR: δ6 6.79-7.03 ppm (singlet, 2H), 3.78-4.14 ppm (triplet, 4H), 1.64-1.92 ppm (multiplet, 4H), 1.37-1.63 ppm (multiplet, 4H), 0.76-1.13 ppm (triplet, 6H), 0.25-0.67 ppm (singlet, 6H). $^{13}$C NMR: δ6 0.362 ppm (2C), 13.84 ppm (2C), 19.20 ppm (2C), 31.28 ppm (2C), 69.23 ppm (2 C), 96.51 ppm (2C), 101.82 ppm (2C), 113.97 ppm (2C), 117.32 ppm (2C), 154.17 ppm (2C). $^{29}$Si NMR: δ−39.33 ppm (1 Si).

EXAMPLE 2

Preparation of Methoxy-Substituted Silylene-Diethynylbenzene Polymers

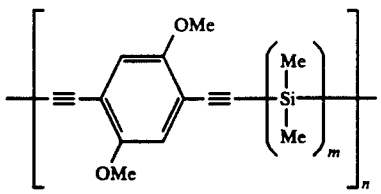

Diethynyltetramethyldisilane (HC≡C—SiMe$_2$—SiMe$_2$—C≡CH, prepared analogously to the preparation of diethynyldimethylsilane as shown below in Example 3, 0.240 g, 1.45 mmol) was combined at room temperature with 1,4-dimethoxy-2,5-diiodobenzene (prepared analogously to the preparation of 1,4-dibutoxy-2,5-diiodobenzene as shown below in Example 4, 0.561 g, 1.45 mmol) in a mixture of benzene (7 mL) and triethylamine (8 mL) containing a catalytic amount of PdCl$_2$(PPh$_3$)$_2$ (15 mg, 2.2×10$^{-2}$ mmol) and CuI (4.4 mg, 2.3×10$^{-2}$ mmol). The mixture was stirred for 16 hours without the addition of heat from an external heat source. The polymer was isolated by filtration and precipitation from methanol. Then it was dissolved in THF and reprecipitated from MeOH. After drying, 0.22 g of polymer was collected. A high molecular weight polymer (m=2) was produced in good yield (50%). Polymerization results are summarized in Table II for this polymer as well as those in which m=1, 3, and 4. The polymers for which m=1, 3, and 4 were prepared by an analogous method using the following starting monomers:

HC≡C—SiMe$_2$—C≡CH for m=1;
HC≡C—SiMe$_2$—SiMe$_2$—C≡CH for m=3; and
HC≡C—SiMe$_2$—SiMe$_2$—SiMe$_2$—C≡CH for m=4.

TABLE II

| Polymer Structure | Yield | Reaction Time (h) | M$_w$ ×10$^{-3}$ | M$_w$/M$_n$ | Solubility |
|---|---|---|---|---|---|
| m = 1 | 88% | 55 | 5.0 | 1.20 | THF, Bz, CHCl$_3$ |
| m = 2 | 50% | 16 | 9.1 | 2.20 | THF, Bz, CHCl$_3$ |
| m = 3 | 60% | 96 | 19.7 | 2.10 | THF, Bz, CHCl$_3$ |
| m = 4 | 53% | 96 | 12.5 | 1.90 | THF, Bz, CHCl$_3$ |

The characterization data for the polymer prepared by this method when m=2 is as follows. $^1$H NMR: δ6.84 ppm (singlet, 2H), 3.73 ppm (singlet, 6H), 0.38 ppm (singlet, 12H). $^{13}$C NMR: δ−2.94 ppm (4C), 56.34 ppm (2C), 98.63 ppm (2C), 103.54 ppm (2C), 113.64 ppm (2C), 116.08 ppm (2C), 154.30 ppm (2C). $^{29}$Si NMR: δ−36.65 ppm (2 Si).

The characterization data for the polymer prepared by this method when m=3 is as follows. $^1$H NMR: δ6.84 ppm (singlet, 2H), 3.73 ppm (singlet, 6H), 0.328 ppm (singlet, 12H), 0.264 ppm (singlet, 6H). $^{29}$Si NMR: δ−33.81 ppm (2Si), −45.93 ppm (1 Si).

The characterization data for the polymer prepared by this method when m=4 is as follows. $^1$H NMR: δ6 6.82 ppm (singlet, 2H), 3.78 ppm (singlet, 4H), 0.29 ppm (singlet, 12H), 0.250 (singlet, 12H). $^{13}$C NMR: δ−5.95 ppm (4C), −1.882 ppm (4C), −56.17 ppm (2C), 99.71 ppm (2C), 103.50 ppm (2C), 113.57 ppm (2C), 115.86 ppm (2C), 154.15 ppm (2C). $^{29}$Si NMR: δ−43.42 ppm (2 Si), −33.42 ppm (2 Si).

The characterization data for the polymer prepared by this method when m=1 is as follows. $^1$H NMR: δ 6.91 ppm (singlet, 2H), 3.79 ppm (singlet, 6H), 0.48 ppm (singlet, 6H). $^{13}$C NMR: δ154.33 ppm (2C), 116.31 ppm (2C), 113.39 ppm (2C), 101.66 ppm (2C), 96.86 ppm (2C), 56.43 ppm (2C), 0.49 ppm (2C). $^{29}$Si NMR: δ−38.99 ppm (1 Si).

EXAMPLE 3

Preparation of Diethynyldimethylsilane

Dimethyldichlorosilane (91 mL, 0.8 mol) was added dropwise over a period of 0.5 hour to a solution of ethynylmagnesium chloride (1.65 mol in 1000 mL THF, prepared from acetylene and 1.65 mole n-butylmagnesium chloride) in an ice bath. The addition rate was slow enough to keep the temperature below 20° C. After addition the mixture was stirred at room temperature overnight. The reaction mixture was cautiously poured into 500 mL (0.5M) cold aqueous HCl solution. The organic layer was separated and washed two more times with dilute aqueous HCl solution. Finally the organic layer was dried over Na$_2$SO$_4$. A product with a boiling point of 83°-88° C. was collected via fractional distillation through a 60 cm column packed with glass helices. After thirty washings with dilute aqueous HCl solution, 70 grams of diethynyldimethylsilane (96% pure by GC, 78% yield) was obtained.

EXAMPLE 4

Preparation of 1,4-Dibutoxy-2,5-diiodobenzene

The following preparation is generally analogous to that reported in *Chemistry Letters*, 795 (1988). To a 1 L round-bottomed flask equipped with a stirring bar, ZnCl$_2$ (10.0 g), acetic acid (600 mL), 1,4-dibutoxybenzene (10.2 g, 0.046 mol, prepared from 1,4-hydroxybenzene in the presence of NaOMe, MeOH, and excess n-butylhalide), and [N(Me)$_3$(CH$_2$Ph)]$^+$ICl$_2^-$ ("BTMICl$_2$," available from Aldrich Chemical Co., 52.1 g, 0.150 mol) were added. After the solution was warmed to 50° C., all of the solids were dissolved. The solution was stirred about 24 hours at 50°-60° C. under an argon atmosphere. From gas chromatographic (GC) analysis, 85% product was formed. After purification by recrystallation from MeOH, 16.0 g (74%) white crystals (needles) with mp=86°-87.5° C. were collected.

All patents, patent documents and publications cited hereinabove are incorporated by reference. The foregoing detailed description has been given for clarity of understanding only and no unnecessary limitations are to be understood therefrom. The invention is not limited to the exact details shown and described, for obvious modifications will occur to those skilled the art.

What is claimed is:

1. An organosilicon polymeric liquid crystal of the formula:

wherein
(a) n≧2;
(b) m=1-6;
(c) R$^1$ and R$^2$ are independently selected from the group consisting of alkyl, alkenyl, aryl, and aralkyl; and
(d) Ar is a substituted arylene.

2. The organosilicon liquid crystal of claim 1 wherein the polymer has a weight average molecular weight of at least about 5,000.

3. The organosilicon liquid crystal of claim 2 wherein the polymer has a polydispersity between about 1.2 and 3.0.

4. The organosilicon liquid crystal of claim 1 wherein the polymer has a weight average molecular weight of between about 5,000 and about 100,000.

5. The organosilicon liquid crystal of claim 1 wherein R$^1$ and R$^2$ are independently selected from the group consisting of (C$_1$-C$_{20}$)alkyl, (C$_2$-C$_{20}$)alkenyl, (C$_6$-C$_{17}$)aryl, and (C$_7$-C$_{20}$)aralkyl.

6. The organosilicon liquid crystal of claim 1 wherein the arylene is selected from the group consisting of a fused-ring aromatic system, a phenylene group, a biphenylene, or a hetero-aromatic system.

7. The organosilicon liquid crystal of claim 6 wherein the arylene is substituted with two functional groups.

8. The organosilicon liquid crystal of claim 6 wherein R$^1$ and R$^2$ are independently selected from the group consisting of (C$_1$-C$_{20}$)alkyl, (C$_2$-C$_{20}$)alkenyl, (C$_6$-C$_{17}$)aryl, and (C$_7$-C$_{20}$)aralkyl.

9. The organosilicon liquid crystal of claim 1 wherein m=1-4.

10. An organosilicon linear polymer of the formula:

wherein
(a) n≧2;
(b) m=1-6;
(c) R$^1$ and R$^2$ are independently selected from the group consisting of alkyl, alkenyl, aryl, and aralkyl; and
(d) Ar is a substituted phenylene.

11. The organosilicon linear polymer of claim 10 wherein the polymer has a weight average molecular weight of at least about 5,000.

12. The organosilicon linear polymer of claim 11 wherein n=2-150.

13. The organosilicon linear polymer of claim 10 wherein R$^1$ and R$^2$ are independently selected from the group consisting of (C$_1$-C$_{20}$)alkyl, (C$_2$-C$_{20}$)alkenyl, (C$_6$-C$_{17}$)aryl, and (C$_7$-C$_{20}$)aralkyl.

14. The organosilicon linear polymer of claim 13 wherein the polymer has a weight average molecular weight of between about 9,000 and about 40,000.

15. The organosilicon linear polymer of claim 10 wherein the polymer has a weight average molecular weight of between about 9,000 and about 40,000.

16. The organosilicon linear polymer of claim 10 wherein m=1-4.

17. The organosilicon linear polymer of claim 16 wherein m=2 and 4.

18. The organosilicon linear polymer of claim 10 wherein the phenylene is disubstituted with functional groups in an ortho- or para- relationship.

19. A process for producing a linear silylene-diethynylarylene polymer having liquid crystalline properties comprising polymerizing a diethynylsilane monomer of the general formula HC≡C—(—SiR$^1$R$^2$)$_m$—C≡CH and a para-dihalo substituted arylene monomer, with an effective amount of a condensation catalyst, wherein each R$^1$ and R$^2$ in the diethynylsilane is independently selected from the group consisting of alkyl, alkenyl, aryl, and aralkyl, and m=1-6.

20. The process of claim 19 wherein the condensation catalyst is a palladium catalyst.

* * * * *